(12) United States Patent
Malikarjuna

(10) Patent No.: US 6,333,440 B1
(45) Date of Patent: Dec. 25, 2001

(54) PROCESS FOR PERFLUOROCYCLOBUTANE PURIFICATION

(75) Inventor: V. N. Malikarjuna, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/825,748

(22) Filed: Apr. 4, 2001

Related U.S. Application Data

(60) Provisional application No. 60/195,855, filed on Apr. 7, 2000.

(51) Int. Cl.[7] .................................................. C07C 17/38
(52) U.S. Cl. .......................................... 570/178; 570/177
(58) Field of Search ..................................... 570/177, 178

(56) References Cited

U.S. PATENT DOCUMENTS

| | | |
|---|---|---|
| 3,541,165 | 11/1970 | Vecchio et al. . |
| 3,632,834 | 1/1972 | Christoph et al. . |
| 4,766,260 | 8/1988 | Manzer et al. . |
| 4,902,838 | 2/1990 | Manzer et al. . |
| 5,001,287 | 3/1991 | Fernandez et al. . |
| 5,036,036 | 7/1991 | Lerou . |
| 5,345,017 | 9/1994 | Rao et al. . |
| 5,444,171 | 8/1995 | Ohno et al. . |
| 5,461,177 | 10/1995 | Manzer et al. . |
| 5,672,784 | 9/1997 | Murphy et al. . |
| 5,763,698 | 6/1998 | Manzer et al. . |
| 6,143,938 | * 11/2000 | Sievert et al. ................. 570/177 |
| 6,147,267 | * 11/2000 | Sievert et al. ................. 570/177 |

FOREIGN PATENT DOCUMENTS

| | | |
|---|---|---|
| 2025145 | 9/1989 | (CA) . |
| 0 455 399 A2 | 6/1991 | (EP) . |
| 0 455 399 A3 | 6/1991 | (EP) . |
| WO99/44973 | 9/1999 | (WO) . |

* cited by examiner

*Primary Examiner*—Alan Siegel

(57) ABSTRACT

A process is disclosed for obtaining octafluorocyclobutane of increased purity from a mixture comprising (a) octafluorocyclobutane and (b) at least one halocarbon impurity which is difficult to separate from octafluorocyclobutane by distillation (e.g., azeotropes of octafluorocyclobutane with such halocarbons). The process involves (1) contacting the mixture with a catalyst in the vapor phase in the presence HCl and/or HF at a temperature sufficient to react component (b) impurity with HCl and/or HF to provide a product mixture comprising halogenated product which is more easily separated from octafluorocyclobutane by distillation than the unreacted impurity; and (2) separating halogenated product obtained in (1) from octafluorocyclobutane by distillation.

10 Claims, No Drawings

PROCESS FOR PERFLUOROCYCLOBUTANE PURIFICATION

This appl. claims benefit of Prov. No. 60/195,855 filed Apr. 7, 2000.

FIELD OF THE INVENTION

This invention relates to processes for the purification of perfluorocyclobutane by the removal of unsaturated and/or saturated halocarbons.

BACKGROUND OF THE INVENTION

Perfluorocyclobutane (c-318 or octafluorocyclobutane, b.p. −6° C.) is a valuable material which can be used as a propellant, etch gas, and fire extinguishant. This compound is typically made by cyclodimerization of tetrafluoroethene (TFE) or is recovered as a co-product from the manufacture of TFE. As a result c-318 may be contaminated with unsaturates such as E- and Z-perfluoro-2-butene (i.e., $CF_3CF$=$CFCF_3$ or PFC-1318my). These compounds are toxic and must be removed prior to commercial use. PFC-1318's are difficult to separate from c-318 by distillation as the boiling points are similar.

Saturated by-products are also typically produced during the c-318 manufacturing process. These include isomers of compounds of the formula $C_2Cl_2F_4$, $C_2HClF_4$ and $C_2H_2F_4$. Some of these impurities form azeotropes with the c-318 and some have similar boiling points. Hence, separation of c-318 from saturated by-products can also be challenging.

U.S. Pat. No. 5,001,287 discloses a process for treating an impure mixture consisting essentially of at least one olefinic impurity and at least one saturated halocarbon by contacting the mixture with a source of hydrogen in the presence of a hydrogenation catalyst (e.g., a catalyst containing a Group VIII metal or rhenium). Perfluorocyclobutane is included among the examples of saturated halocarbons.

U.S. Pat. No. 5,763,698 discloses a process for reducing the fluorine content of hydrochlorofluorocarbons and hydrofluorocarbons by reacting these compounds with HCl in the vapor phase at an elevated temperature in the presence of a catalyst.

U.S. Pat. No. 5,345,017 discloses a process for reducing the fluorine content of acyclic fluorocarbons and chlorofluorocarbons by reacting these compounds with HCl in the vapor phase at an elevated temperature in the presence of a catalyst. In Example 8, a linear perfluorocarbon, perfluoropropane is converted to chlorofluoropropanes.

There is a need for alternative methods of purification.

SUMMARY OF THE INVENTION

This invention provides a process for obtaining octafluorocyclobutane of increased purity from a mixture comprising (a) octafluorocyclobutane and (b) at least one halocarbon impurity which is difficult to separate from octafluorocyclobutane by distillation (e.g., azeotropes of octafluorocyclobutane with such halocarbons). The process comprises (1) contacting the mixture with a catalyst in the vapor phase in the presence of at least one hydrogen halide selected from the group consisting of HCl and HF at a temperature sufficient to react component (b) impurity with said hydrogen halide to provide a product mixture comprising halogenated product which is more easily separated from octafluorocyclobutane by distillation than the unreacted impurity; and (2) separating halogenated product obtained in (1) from octafluorocyclobutane by distillation.

DETAILS OF THE INVENTION

Octafluorocyclobutane is typically produced during the manufacture of tetrafluoroethylene and hexafluoropropylene by the pyrolysis of chlorodifluoromethane as discussed in U.S. Pat. No. 5,672,784. Octafluorocyclobutane can also be produced by the electrolysis of 1,1,2,2-tetrafluorocyclobutane as disclosed in European Patent Publication No. 0 455 399. During the electrolysis process, the major product (about 62 mole %) is octafluorocyclobutane. However, minor amounts (about 7 mole %) of product with an intermediate degree of fluorination are also found.

Processes used to produce c-318 may simultaneously produce a variety of halogenated impurities in the c-318 product stream (see for example PCT International Publication No. WO 99/44973). Examples of halogenated impurities that may be found in a c-318 production stream include linear and cyclic, saturated and unsaturated, perfluorocarbons (PFCs), chlorofluorocarbons (CFCs), hydrochlorofluorocarbons (HCFCs), hydrofluorocarbons (HFCs), and hydrochlorocarbons (HCCs). Representative examples from these classes of halogenated impurities include: PFC-31-10 (normal iso-$C_4F_{10}$, perfluorobutane isomers), PFC-41-12 ($C_5F_{12}$, perfluoropentane isomers), PFC-1318my (cis and trans-$CF_3CF$=$CFCF_3$), PFC-1318c ($CF_3CF_2CF$=$CF_2$), PFC-1216 (HFP or $CF_3CF$=$CF_2$), PFC-1114 (TFE or $CF_2$=$CF_2$) perfluoroisobutene ($CF_2$=$C(CF_3)_2$), CFC-114 ($CF_2ClCF_2Cl$), CFC-114a ($CFCl_2CF_3$), CFC-216ba ($CF_3CFClCF_2Cl$), CFC-217ba ($CF_3CClFCF_3$), CFC-1113 (CClF=$CF_2$), HCFC-22 ($CHClF_2$), HCFC-21 ($CHCl_2F$), HCFC-124 ($CHFClCF_3$), HCFC-124a ($CClF_2CHF_2$), HFC-134 ($CHF_2CHF_2$), HFC-134a ($CH_2FCF_3$), HFC-152a ($CH_3CF_2H$), HFC-125 ($CF_3CF_2H$), HFC-227ca ($CF_3CF_2CHF_2$), HFC-227ea ($CF_3CHFCF_3$), HFC-1225zc ($CF_3CH$=$CF_2$), HFC-236ca ($CHF_2CF_2CHF_2$), HFC-236ea ($CHF_2CHFCF_3$), HFC-236fa ($CF_3CH_2CF_3$), HCC-30 ($CH_2Cl_2$), HCC-40 ($CH_3Cl$), and HCC-160 ($CH_3CH_2Cl$).

Compounds having a boiling point within about 15° C. of the c-318 boiling point are difficult to separate from c-318 by distillation, especially within about 10° C., and more especially within about 5° C. Compounds which form azeotropes or azeotrope-like compositions with c-318 are also difficult to separate by distillation.

Among the unsaturated impurities which are difficult to separate from c-318 and which may be reacted with hydrogen halides are the acyclic compounds selected from $C_2HClF_2$, $C_2H_2ClF$, $C_3ClF_5$, $C_3HF_5$, $C_4F_8$, $C_4H_2F_6$, $C_4F_6$ and the cyclic compounds selected from c-$C_4F_6$ and c-$C_5F_8$. This invention provides a process for obtaining c-318 of increased purity from a mixture comprising c-318 and at least one of said unsaturated impurities. Of note is a process for obtaining c-318 of increased purity from a mixture comprising c-318 and $C_4F_8$. Also of note is a process for obtaining c-318 of increased purity from a mixture comprising c-318 and $C_3ClF_5$. Also of note is a process for obtaining c-318 of increased purity from a mixture comprising c-318 and $C_3HF_5$. Of particular note are processes where HCl is reacted with these unsaturated impurities.

Among the saturated impurities which are difficult to separate from c-318 and which may be reacted with hydrogen halides are the acyclic compounds selected from $CHCl_2F$, $C_2Cl_2F_4$, $C_2HClF_4$, $C_2H_2F_4$, $C_2H_4F_2$, $C_3ClF_7$, $C_3HF_7$, $C_3HClF_6$, $C_3HClF_6$, $C_3H_2F_6$ and $C_4F_{10}$. This invention provides a process for recovering c-318 from a mixture comprising c-318 and at least one of said saturated impurities. Of note is a process for obtaining c-318 of increased purity from a mixture comprising c-318 and $C_2Cl_2F_4$. Also of note is a process for obtaining c-318 of increased purity from a mixture comprising c-318 and $C_2HClF_4$. Also of note is a process for obtaining c-318 of increased purity from a mixture comprising c-318 and $C_2H_2F_4$. Of particular note are processes where HCl is reacted with $C_2Cl_2F_4$, $C_2HClF_4$ and/or $C_2H_2F_4$ and processes where HF is reacted with $C_2HClF_4$.

It will be evident that not all of the component (b) impurity must be reacted in order to obtain increased c-318 purity. Generally, where reaction of the component (b) impurity results in a halogenated product that boils at a lower temperature than c-318, this low-boiling halogenated product may be selectively distilled from the product mixture to leave an octafluorocyclobutane-containing composition of increased c-318 purity. Generally, where reaction of the component (b) impurity results in a halogenated product that boils at a higher temperature than c-318, an octafluorocyclobutane-containing composition of increased c-318 purity may be selectively distilled from the product mixture to leave a composition rich in this high-boiling halogenated product. In any case, it is often desirable to react at least 50 mole percent of the component (b) impurity in accordance with this invention.

Sometimes, substantially all of the component (b) impurity is reacted in accordance with this invention such that c-318 can be recovered by distillation. Of note is a process for recovering octafluorocyclobutane from a mixture comprising c-318 and $C_4F_8$. Also of note is a process for recovering octafluorocyclobutane from a mixture comprising c-318 and $C_3ClF_5$. Also of note is a process for recovering octafluorocyclobutane from a mixture comprising c-318 and $C_3HF_5$. Also of note is a process for recovering octafluorocyclobutane from a mixture comprising c-318 and $C_2Cl_2F_4$. Also of note is a process for recovering octafluorocyclobutane from a mixture comprising c-318 and $C_2HClF_4$. Also of note is a process for recovering octafluorocyclobutane from a mixture comprising c-318 and $C_2H_2F_4$.

Several of the halocarbon impurities noted above form azeotropic or azeotrope-like mixtures with c-318, making high-recovery efficiency of substantially pure c-318 from mixtures containing them by distillation particularly difficult. Impurities that form azeotropic or azeotrope-like mixtures with c-318 include each of HCFC-124, HCFC-124a, HFC-134, HFC-134a and HFC-152a. This invention provides a process for recovering c-318 from these azeotrope or azeotrope-like mixtures. Of note is a process for recovering c-318 from an azeotropic or azeotrope-like mixture of c-318 with $C_2HClF_4$ (i.e., HCFC-124 and/or HCFC-124a) wherein $C_2HClF_4$ is reacted with HF to produce $C_2HF_5$; and wherein essentially pure c-318 and essentially pure $C_2HF_5$ is recovered. Inasmuch as $C_2HF_5$ can form an azeotrope with HF, further separation of $C_2HF_5$ from HF may be required in order to obtain essentially pure $C_2HF_5$. HF removal can be accomplished by conventional means. This invention thus provides a method of obtaining essentially pure c-318 and essentially pure HFC-125 from an azeotrope or azeotrope-like mixture of c-318 and $C_2HClF_4$ which comprises contacting the mixture with a catalyst in the vapor phase in the presence of HF at a temperature sufficient to react $C_2HClF_4$ with HF to provide a product mixture comprising $C_2HF_5$; (2) separating $C_2HF_5$; from the product mixture by distillation and removing azeotropically combined HF therefrom; and (3) separating essentially pure octafluorocyclobutane from the product mixture by distillation.

It is noted that for azeptropic mixtures, not all of the component (b) impurity needs to be reacted in order to recover essentially pure c-318. For these embodiments, after reaction of the component (b) impurity with hydrogen halide in accordance with this invention, halogenated product may be separated from the product mixture by distillation and essentially pure c-318 may also be obtained from said product mixture by distillation. Of course, if not all of the component (b) impurity is reacted, some of the c-318 may remain in azeotropic mixture with the unreacted halocarbon.

Suitable catalysts which can be used include vapor phase fluorination catalysts. Catalysts which may be used in accordance with this invention include metals (including elemental metals, metal oxides and/or other metal salts); alumina; fluorided alumina; aluminum fluoride; metals on alumina; metals on aluminum fluoride; magnesium fluoride on aluminum fluoride; metals on fluorided alumina; alumina on carbon; aluminum fluoride on carbon; fluorided alumina on carbon; metals on carbon; chromium catalysts (e.g., $Cr_2O_3$ by itself or with other metals such as Mg and/or Zn); mixtures of metals, aluminum fluoride, and graphite; and chromium-magnesium optionally on graphite.

Suitable metals for use as catalysts (optionally on alumina, aluminum fluoride, fluorided alumina or carbon) include chromium, Groups 8, 9 and 10 metals (i.e., iron, cobalt, nickel, ruthenium, rhodium, palladium, osmium, iridium, platinum), Group 7 metals (i.e., manganese, rhenium), Group 3 metals (i.e., scandium, yttrium, lanthanum), Group 11 metals (i.e., copper, silver, gold), zinc and/or metals having an atomic number of 58 through 71 (cerium, praseodymium, neodymium, promethium, samarium, europium, gadolonium, terbium, dysprosium, holmium, eribium, thulium, ytterbium or lutetium). Preferably, when used with a support, the total metal content of the catalyst will be from about 0.1 to 20 percent by weight; typically, from about 0.1 to 10 percent by weight.

Fluorided alumina and aluminum fluoride can be prepared as described in U.S. Pat. No. 4,902,838. By aluminum fluoride is meant at least one of aluminum fluoride (e.g., alpha-$AlF_3$, beta-$AlF_3$, delta-$AlF_3$, eta-$AlF_3$, gamma-$AlF_3$, kappa-$AlF_3$ and/or theta-$AlF_3$). By fluorided alumina is meant a composition comprising aluminum, oxygen and fluorine. The fluoride content of the fluorided alumina can vary over a wide range, from about 0.001% to about 67.8% by weight.

Metals on aluminum fluoride and metals on fluorided alumina can be prepared by procedures described in U.S. Pat. No. 4,766,260. Catalysts comprising chromium are well known in the art (see e.g., U.S. Pat. No. 5,036,036). Chromium supported on alumina can be prepared as described in U.S. Pat. No. 3,541,165. Chromium supported on carbon can be prepared as described in U.S. Pat. No. 3,632,834. Catalysts comprising chromium and magnesium may be prepared as described in Canadian Patent No. 2,025,145. Other metals and magnesium optionally on graphite can be prepared in a similar manner to the latter patent. Preferred catalysts include catalysts comprising fluorided alumina, catalysts comprising aluminum fluoride and catalysts comprising chromium oxide which is fluorided prior to use.

The reaction of impurities in the octafluorocyclobutane with HCl and/or HF is suitably conducted in the presence of the catalysts of this invention at a temperature within the range of from about 250° C. to 450° C., preferably from about 300° C. to 400° C., and most preferably from about 325° C. to about 375° C. The contact time is typically from about 0.1 to about 120 seconds, preferably from about 1 to about 60 seconds.

Preferably, the mole ratio of hydrogen halide (i.e., HCl and/or HF) to c-318 present at the start of catalyst contact is at least about 1:1. The amount of HCl and/or HF is also preferably at least a stoichiometric amount with respect to the component (b) impurity contained in the starting mixture. Typically, the molar ratio of total impurity to c-318 is less than 1:1 (e.g., from about 1:999 to 1:1) and the molar ratio of HCl and/or HF to the octafluorocyclobutane ranges from about 1:1 to about 100:1, preferably from about 2:1 to about 50:1, and more preferably from about 3:1 to about 20:1.

Typically, halogen halide is mixed with the starting mixture containing the c-318 and component (b) impurity. However in some cases, the starting mixture may itself contain substantial amounts of the desired hydrogen halide. For example, the c-318 purification of this invention can be used to increase the purity of c-318 from a mixture that is produced during the manufacture of tetrafluoroethylene and c-318 (and optionally hexafluoropropylene) by the pyrolysis of chlorodifluoromethane or mixtures of chlorodifluoromethane and chlorotetrafluoroethane. Typically, HCl is also produced by such pyrolysis. Of note are embodiments where the mixture contacted with catalyst is produced as a result of that pyrolysis, and the hydrogen halide present during catalyst contact comprises HCl which is also produced by the pyrolysis.

In general, with a given catalyst composition, the higher the temperature and the longer the contact time, the greater is the conversion of the unsaturated and saturated by-products and the greater is the production of products from the reaction of the by-products with HCl and/or HF. Remarkably, very little of the c-318 reacts with either hydrogen halide.

The reaction products may normally be separated by conventional techniques, such as distillation. Some of the reaction products will have desired properties for commercial use by themselves (e.g., $C_2HF_5$ from $C_2HClF_4$) or as intermediates for making other commercial products. Others, such as $CHCl=CCl_2$, $CCl_2=CCl_2$, $CHCl_3$, etc. can be recycled back to reactors which are being used for the synthesis of hydrofluorocarbons and hydrohalofluorocarbons.

The reaction of unsaturated impurity (i.e., one or more unsaturated compounds) and saturated impurity (i.e., one or more saturated compounds) in impure octafluorocyclobutane by contacting the mixture with catalyst in the presence of the HCl and/or HF may be conducted in any suitable reactor, including fixed and fluidized bed reactors. The reaction vessel should be constructed from materials that are resistant to the corrosive effects of hydrogen chloride and hydrogen fluoride such as Inconel™ nickel alloy and Hastelloy™ nickel alloy.

Pressure is not critical. Atmospheric and superatmospheric pressures are the most convenient and are therefore preferred.

EXAMPLES

In the following illustrative examples all percentages are molar and all temperatures are Celsius unless otherwise stated.

General Procedure for Fluorided Alumina Catalyst

A reactor, (a 0.5 inch (1.3 cm) ID by 12 inch (30.5 cm) long Inconel™ nickel alloy pipe) was charged with the amount of catalyst as described in the following examples, and placed in a sand bath. The bath was gradually heated to 175° C. while $N_2$ gas at a flow rate of 50 cc/min was passed through the reactor for about 30 minutes. A 1:1 molar ratio of hydrogen fluoride and nitrogen (total flow 100 cc/min.) was passed through the reactor. The temperature was gradually raised to 350° C. while increasing the $HF:N_2$ molar ratio to 4:1. The reactor was kept at 350° C. for about 2 hours. The HF flow was then halted, the reactor purged with $N_2$ and then brought to the desired operating temperature. Thereafter, the $N_2$ flow was stopped and the other reactant flows were started. The flows were adjusted to give the indicated molar ratios and contact times in the Examples.

The reactor effluent was sampled on-line with a Hewlett Packard HP 5890 gas chromatograph using a 20 foot (6.1 m) long, one-eighth inch (3.2 mm) diameter column containing Krytox™ perfluorinated polyether on an inert support, and a helium flow of 35 cc/mm. Gas chromatographic conditions were 70° C. for three minutes followed by temperature programming to 180° C. at a rate of 6° C./minute.

| LEGEND | |
|---|---|
| 112 is $CCl_2FCCl_2F$ | 112a is $CCl_2FCF_3$ |
| 113/a is a mixture of $CCl_2FCClF_2$ and $CCl_3CF_3$ | |
| 114 is $CClF_2CClF_2$ | 114a is $CCl_2FCF_3$ |
| 115 is $CClF_2CF_3$ | 123 is $CHCl_2CF_3$ |
| 123a is $CHClFCClF_2$ | 123b is $CHF_2CCl_2F$ |
| 124 is $CHClFCF_3$ | 124a is $CHF_2CClF_2$ |
| 125 is $CHF_2CF_3$ | 132a is $CHF_2CHCl_2$ |
| 132b is $CH_2ClCClF_2$ | 133 is $CHClFCHF_2$ |
| 133a is $CH_2ClCF_3$ | 134 is $CHF_2CHF_2$ |
| 134a is $CH_2FCF_3$ | PCE is $CCl_2=CCl_2$ |
| TCE is $CHCl=CCl_2$ | 1111 is $CCl_2=CClF$ |
| 1112a is $CCl_2=CF_2$ | 1121 is $CHCl=CClF$ |
| 1316 is $CF_3CCl=CClCF_3$ | 1317 is $CF_3CCl=CFCF_3$ |
| c318 is perfluorocyclobutane | 1318my is one of E- or Z-$CF_3CF=CFCF_3$ |

Example 1

The organic feed to the reactor contained 99.61% c-318, and 0.32% of the isomers of 1318my. The catalyst, 2.79 g (4 cc) was alumina which was treated with HF prior to use according to the General Procedure. The contact time, based on empty reactor volume was 10 seconds. Table 1 shows the results obtained over a 9 hour period.

TABLE 1

| Hrs. | T (° C.) | Mole Ratio HCl:c318 | % c318 | % 1318my | % 1318my | % TCE | % Unknowns[a] |
|---|---|---|---|---|---|---|---|
| 0.5 | 275 | 2 | 99.54 | 0.38 | 0.06 | 0.00 | 0.02 |
| 1.5 | 300 | 2 | 99.56 | 0.37 | 0.06 | 0.00 | 0.01 |
| 2.5 | 325 | 2 | 99.57 | 0.33 | 0.08 | 0.00 | 0.02 |
| 3.0 | 350 | 2 | 99.64 | 0.23 | 0.09 | 0.00 | 0.04 |
| 4.0 | 375 | 2 | 99.80 | 0.10 | 0.04 | 0.04 | 0.02 |
| 5.0 | 400 | 2 | 99.89 | 0.00 | 0.00 | 0.06 | 0.05 |
| 6.0 | 425 | 2 | 99.95 | 0.00 | 0.00 | 0.01 | 0.04 |
| 7.0 | 450 | 2 | 99.93 | 0.00 | 0.00 | 0.03 | 0.04 |
| 8.0 | 450 | 4 | 99.51 | 0.00 | 0.00 | 0.16 | 0.33 |
| 9.0 | 450 | 4 | 99.58 | 0.00 | 0.00 | 0.31 | 0.11 |

[a]Unknowns include PCE.

Examination of the data shows that the two isomers of 1318 (b.p. of 0 and 1° C.), which boil very closely to c-318 (b.p. is −6° C.) and hence are difficult to completely remove by distillation are converted to higher boiling compounds.

Example 2

This example was carried out to determine whether 124 which forms an azeotrope with c-318 can be selectively converted to higher boiling compounds by reaction with HCl. The contact time was 5 seconds. The catalyst used was the same as that used in Example 1. Table 2 summarizes data obtained at different operating temperatures.

Procedure, except that the final temperature was 400° C. The ratio of HCl:c318:114 isomer mixture was 4:1:0.15. The contact time was ten seconds. Results obtained are tabulated in Table 4.

TABLE 2

| T (° C.) | 124a | 124 | c318 | 1318my | 1318my | 123 | 1112a | 113a | 1111 | PCE | $C_4Cl_6$ | Unknowns |
|---|---|---|---|---|---|---|---|---|---|---|---|---|
| Feed | 0.05 | 10.48 | 89.03 | 0.38 | 0.04 | 0.00 | 0.00 | 0.00 | 0.00 | 0.00 | 0.00 | 0.01 |
| 300 | 0.05 | 10.22 | 89.23 | 0.35 | 0.06 | 0.07 | 0.00 | 0.00 | 0.00 | 0.00 | 0.00 | 0.01 |
| 325 | 0.05 | 10.14 | 89.08 | 0.32 | 0.07 | 0.29 | 0.00 | 0.00 | 0.00 | 0.00 | 0.00 | 0.04 |
| 350 | 0.05 | 9.73 | 89.09 | 0.23 | 0.09 | 0.78 | 0.00 | 0.00 | 0.00 | 0.00 | 0.00 | 0.03 |
| 375 | 0.05 | 8.81 | 89.13 | 0.17 | 0.07 | 1.67 | 0.00 | 0.01 | 0.02 | 0.00 | 0.00 | 0.07 |
| 400 | 0.10 | 7.40 | 89.00 | 0.08 | 0.03 | 2.71 | 0.08 | 0.04 | 0.27 | 0.10 | 0.12 | 0.06 |
| 425 | 0.15 | 5.98 | 88.96 | 0.03 | 0.01 | 2.72 | 0.35 | 0.11 | 1.14 | 0.31 | 0.10 | 0.13 |
| 450 | 0.15 | 4.48 | 88.89 | 0.00 | 0.00 | 2.38 | 0.07 | 0.17 | 2.50 | 1.00 | 0.00 | 0.36 |

Examination of the data shows that 124 can be converted to higher boiling materials by reaction with HCl under conditions where c-318 is essentially unchanged.

Example 3

Example 2 was substantially repeated except that 124a was used instead of 124 since this also has been reported to form an azeotrope with c-318. The results obtained are summarized in Table 3.

TABLE 3

| T (° C.) | 124a | 124 | c318 | 1318my | 114 | 1318my | 123 | 1112a | 113/a | 1111 | PCE | $C_4Cl_6$ | Unknowns[a] |
|---|---|---|---|---|---|---|---|---|---|---|---|---|---|
| Feed | 9.59 | 0.36 | 89.62 | 0.37 | 0.02 | 0.04 | 0.00 | 0.00 | 0.00 | 0.00 | 0.00 | 0.00 | 0.01 |
| 350 | 8.80 | 0.58 | 89.78 | 0.21 | 0.02 | 0.08 | 0.12 | 0.00 | 0.00 | 0.14 | 0.17 | 0.00 | 0.10 |
| 375 | 6.07 | 2.00 | 89.67 | 0.10 | 0.02 | 0.04 | 0.79 | 0.04 | 0.02 | 0.45 | 0.75 | 0.00 | 0.03 |
| 400 | 2.57 | 3.77 | 89.15 | 0.04 | 0.02 | 0.02 | 1.66 | 0.07 | 0.08 | 0.75 | 1.48 | 0.31 | 0.07 |
| 425 | 0.95 | 4.04 | 88.94 | 0.02 | 0.08 | 0.00 | 1.78 | 0.13 | 0.14 | 1.43 | 2.07 | 0.33 | 0.07 |
| 425 | 1.02 | 4.09 | 88.92 | 0.02 | 0.08 | 0.00 | 1.75 | 0.13 | 0.12 | 1.37 | 2.02 | 0.39 | 0.10 |

[a]Unknowns include 123a and 123b.

Examination of Table 3 shows that 124a also reacts with HCl and the c318 is essentially unchanged. The data also

TABLE 4

| T (° C.) | 115 | c318 | 1318my | 114 | 114a | 1318my | 1112a | 113 | 113a | 1111 | TCE | PCE | Unknowns[a] |
|---|---|---|---|---|---|---|---|---|---|---|---|---|---|
| Feed | 0.00 | 89.29 | 0.24 | 9.29 | 1.12 | 0.03 | 0.00 | 0.00 | 0.00 | 0.00 | 0.00 | 0.00 | 0.03 |
| 250 | 0.00 | 89.55 | 0.15 | 9.26 | 0.86 | 0.05 | 0.03 | 0.00 | 0.01 | 0.00 | 0.00 | 0.00 | 0.09 |
| 300 | 0.00 | 89.98 | 0.07 | 9.19 | 0.42 | 0.03 | 0.10 | 0.01 | 0.08 | 0.00 | 0.00 | 0.04 | 0.06 |
| 325 | 0.00 | 90.17 | 0.02 | 9.30 | 0.00 | 0.01 | 0.16 | 0.02 | 0.13 | 0.04 | 0.02 | 0.08 | 0.04 |
| 350 | 0.06 | 89.72 | 0.00 | 4.30 | 1.34 | 0.00 | 0.65 | 0.24 | 2.48 | 0.18 | 0.05 | 0.88 | 0.12 |
| 375 | 0.44 | 89.15 | 0.01 | 0.72 | 2.52 | 0.00 | 0.60 | 0.35 | 4.15 | 0.17 | 0.00 | 1.71 | 0.18 |
| 400 | 1.22 | 88.96 | 0.01 | 0.35 | 2.14 | 0.00 | 0.50 | 0.33 | 3.41 | 0.17 | 0.00 | 2.74 | 0.18 |

[a]Unknowns include 112 shows that even in the presence of HCl, 124a isomerizes to 124 over the fluorided alumina catalyst employed.

Example 4

The organic feed material to the reactor contained c-318, 114, and 114a. The catalyst employed was 12 cc (8.04 g) of 10/20 mesh (2.0/0.84 mm) gamma alumina which was fluorided prior to use using the above-described General Examination of the data shows that both isomers of 114 (114 b.p. is 3.6° C. and 114a b.p. is 3.0° C.) which are very difficult to separate completely from c-318 (b.p. is −6° C.) because of closeness of boiling points react with HCl under the conditions of the experiment and are converted to higher boiling materials.

Example 5

Example 4 was substantially repeated except that the organic feed to the reactor contained c-318 and 134. The organic to HCl ratio was the same as that in Example 4. The catalyst was the one used in Example 4 and the contact time was ten seconds. Data obtained are summarized in Table 5.

TABLE 5

| T (° C.) | 134 | c318 | 113a | 133 | 1318my | 1318my | 132a | 1121 | TCE | 130 | Unknowns[a] |
|---|---|---|---|---|---|---|---|---|---|---|---|
| Feed | 11.00 | 88.70 | 0.00 | 000 | 0.24 | 0.03 | 0.00 | 0.00 | 0.00 | 0.00 | 0.03 |
| 250 | 8.80 | 88.84 | 0.07 | 0.52 | 0.19 | 0.05 | 0.24 | 0.00 | 1.18 | 0.00 | 0.10 |
| 275 | 9.02 | 88.86 | 0.00 | 0.71 | 0.21 | 0.04 | 0.40 | 0.07 | 0.60 | 0.06 | 0.03 |
| 300 | 6.80 | 88.79 | 0.14 | 0.69 | 0.17 | 0.06 | 0.53 | 0.22 | 2.52 | 0.03 | 0.04 |
| 325 | 1.94 | 88.90 | 0.49 | 0.13 | 0.10 | 0.04 | 0.09 | 0.24 | 7.74 | 0.05 | 0.29 |

[a]Unknowns include 1316

The data show that 134 which has been reported to form an azeotrope with c-318 can be selectively reacted with HCl to form higher boiling chlorine-containing compounds.

Example 6

Example 5 was substantially repeated except that the organic feed to the reactor contained c-318 and 134a. It has been reported that 134a forms an azeotrope with c-318. The results obtained are tabulated in Table 6.

TABLE 6

| T (° C.) | 134a | c318 | 133a | 1318my | 1318my | 1121 | 1121 | TCE | Unknowns[a] |
|---|---|---|---|---|---|---|---|---|---|
| Feed | 11.81 | 87.89 | 0.00 | 0.24 | 0.03 | 0.00 | 0.00 | 0.00 | 0.03 |
| 300 | 5.96 | 88.24 | 3.53 | 0.14 | 0.05 | 0.16 | 0.15 | 1.64 | 0.07 |
| 300 | 6.00 | 88.32 | 3.50 | 0.14 | 0.05 | 0.16 | 0.16 | 1.56 | 0.07 |
| 325 | 3.65 | 88.20 | 3.62 | 0.11 | 0.05 | 0.24 | 0.26 | 3.70 | 0.12 |
| 325 | 3.40 | 88.24 | 3.55 | 0.11 | 0.05 | 0.23 | 0.25 | 4.03 | 0.08 |

[a]Unknowns include 132b, 1317 and 1316

The data show that it is possible to convert azeotropically combined 134a from c-318 by the above reaction.

Example 7

This Example illustrates that 124a which can be present as an azeotrope with c-318 can be selectively fluorinated to 125 using HF and a fluorination catalyst. The catalyst used was 13.34 g (10 cc) of chromium oxide of 10/20 mesh (2.0/0.84 mm). It was activated with HF prior to use as follows. A ⅝" (1.6 cm) I.D. Inconel™ nickel alloy reactor was charged with the chrome oxide and heated to 175° C. in a flow of nitrogen (25 cc/min) for about 2 hours. A 2:1 molar ratio of nitrogen and HF was started through the reactor (total flow 100 mL/min). After one hour under these conditions, the molar ratio of nitrogen to HF was adjusted to 1:3 and the temperature increased gradually over a 3 hour period to 425° C. The reactor was then brought back to the desired operating temperature, the flow of HF and nitrogen stopped and the flow of reactants started. The HF:c318:124a mole ratio was 4:1:0.15 and the contact time was ten seconds. The results obtained at specific intervals during a 26 hour period have been tabulated in Table 7.

TABLE 7

| Hrs | T (° C.) | 125 | 124a | 124 | c318 | 1318my | 1318my | Unknowns[a] |
|---|---|---|---|---|---|---|---|---|
| Feed | | 0.00 | 11.76 | 0.28 | 87.44 | 0.36 | 0.04 | 0.12 |
| 15.0 | 300 | 4.53 | 6.18 | 0.19 | 88.71 | 0.26 | 0.07 | 0.06 |
| 17.0 | 300 | 4.75 | 6.00 | 0.18 | 88.70 | 0.25 | 0.07 | 0.06 |
| 19.0 | 300 | 4.83 | 5.89 | 0.19 | 88.70 | 0.25 | 0.07 | 0.06 |

TABLE 7-continued

| Hrs | T (° C.) | 125 | 124a | 124 | c318 | 1318my | 1318my | Unknowns[a] |
|---|---|---|---|---|---|---|---|---|
| 25.0 | 350 | 11.48 | 0.03 | 0.12 | 87.93 | 0.17 | 0.07 | 0.21 |
| 26.0 | 350 | 11.51 | 0.03 | 0.12 | 87.92 | 0.17 | 0.07 | 0.18 |

[a]Unknowns include 114, 114a, 123 1317 and 1316.

Example 8

Example 7 was substantially repeated using the same catalyst as used in Example 7. The organic feed material contained c-318 and 124. The results obtained are summarized in Table 8.

TABLE 8

| Hrs. | T (° C.) | 125 | 124 | c318 | 1318my | 1318my | 123 | Unknowns[a] |
|---|---|---|---|---|---|---|---|---|
| Feed | | 0.00 | 10.53 | 89.03 | 0.29 | 0.04 | 0.00 | 0.11 |
| 1.0 | 275 | 0.50 | 9.69 | 89.36 | 0.28 | 0.04 | 0.00 | 0.12 |
| 19.0 | 300 | 4.91 | 5.34 | 89.24 | 0.24 | 0.07 | 0.13 | 0.06 |
| 21.0 | 300 | 4.89 | 5.25 | 89.34 | 0.25 | 0.07 | 0.13 | 0.06 |
| 24.0 | 325 | 9.57 | 0.86 | 89.15 | 0.22 | 0.09 | 0.06 | 0.05 |

TABLE 8-continued

| Hrs. | T (° C.) | 125 | 124 | c318 | 1318my | 1318my | 123 | Un-knowns[a] |
|---|---|---|---|---|---|---|---|---|
| 25.0 | 325 | 9.75 | 0.79 | 89.04 | 0.21 | 0.09 | 0.06 | 0.06 |
| 28.0 | 350 | 10.86 | 0.10 | 88.65 | 0.16 | 0.07 | 0.01 | 0.15 |
| 29.0 | 350 | 10.54 | 0.10 | 88.98 | 0.16 | 0.06 | 0.01 | 0.15 |

[a]Unknowns include 115, 124a, 1317 and 1316.

Examination of the data in Tables 7 and 8 show that azeotropically combined isomers of $C_2HClF_4$ with c-318 can be converted in high selectivity to 125 (b.p. −48.5° C.) which can subsequently be separated from c-318 (b.p. −6° C.) by distillation to provide both highly pure c-318 and highly pure 125.

What is claimed is:

1. A process for obtaining octafluorocyclobutane of increased purity from a mixture comprising (a) octafluorocyclobutane and (b) at least one halocarbon impurity which is difficult to separate from octafluorocyclobutane by distillation, comprising:
   (1) contacting the mixture with a catalyst in the vapor phase in the presence of at least one hydrogen halide selected from the group consisting of HCl and HF at a temperature sufficient to react component (b) impurity with said hydrogen halide to provide a product mixture comprising halogenated product which is more easily separated from octafluorocyclobutane by distillation than the unreacted impurity; and
   (2) separating halogenated product obtained in (1) from octafluorocyclobutane by distillation.

2. The process of claim 1 wherein the mole ratio of hydrogen halide to octafluorocyclobutane present at the start of catalyst contact is at least about 1:1.

3. The process of claim 2 wherein the mixture comprising (a) and (b) is an azeotrope or azeotrope-like mixture; and wherein after reaction of the component (b) impurity with hydrogen halide, halogenated product is separated from the product mixture by distillation and essentially pure octafluorocyclobutane is also obtained from said product mixture by distillation.

4. The process of claim 2 wherein substantially all of the component (b) impurity is reacted such that octafluorocyclobutane can be recovered by distillation.

5. The process of claim 4 wherein octafluorocyclobutane is recovered from a mixture comprising octafluorocyclobutane and $C_4F_8$, a mixture comprising octafluorocyclobutane and $C_3ClF_5$, a mixture comprising octafluorocyclobutane and $C_3HF_5$, a mixture comprising octafluorocyclobutane and $C_2Cl_2F_4$, a mixture comprising octafluorocyclobutane and $C_2HClF_4$, or a mixture comprising octafluorocyclobutane and $C_2H_2F_4$.

6. A process for increasing the purity of octafluorocyclobutane from a mixture comprising (a) octafluorocyclobutane and (b) at least one halocarbon impurity which is difficult to separate from octafluorocyclobutane by distillation which is produced during the manufacture of tetrafluoroethylene, octafluorocyclobutane and optionally hexafluoropropylene by the pyrolysis of chlorodifluoromethane or mixtures of chlorodifluoromethane and chlorotetrafluoroethane, characterized by:
   (1) contacting the mixture with a catalyst in the vapor phase in the presence of at least one hydrogen halide selected from the group consisting of HCl and HF at a temperature sufficient to react component (b) impurity with said hydrogen halide to provide a product mixture comprising halogenated product which is more easily separated from octafluorocyclobutane by distillation than the unreacted impurity; and
   (2) separating halogenated product obtained in (1) from octafluorocyclobutane by distillation.

7. The process of claim 6 wherein the mole ratio of hydrogen halide to octafluorocyclobutane present at the start of catalyst contact is at least about 1:1.

8. The process of claim 7 wherein the hydrogen halide present during catalyst contact comprises HCl which is also produced by the pyrolysis.

9. A method of obtaining essentially pure octafluorocyclobutane and essentially pure $C_2HF_5$ from an azeotrope or azeotrope-like mixture of octafluorocyclobutane and $C_2HClF_4$, comprising:
   (1) contacting the mixture with a catalyst in the vapor phase in the presence of HF at a temperature sufficient to react $C_2HClF_4$ with HF to provide a product mixture comprising $C_2HF_5$;
   (2) separating $C_2HF_5$ from the product mixture by distillation and removing azeotropically combined HF therefrom; and
   (3) separating essentially pure octafluorocyclobutane from the product mixture by distillation.

10. The process of claim 9 wherein the mole ratio HF to octafluorocyclobutane present at the start of catalyst contact is at least about 1:1.

* * * * *